(12) United States Patent
Thacker

(10) Patent No.: US 9,724,231 B2
(45) Date of Patent: Aug. 8, 2017

(54) HEATING AND/OR COOLING ASSEMBLY

(71) Applicant: Greybull Innovation Ltd, Leicester (GB)

(72) Inventor: Darran Ainsley Thacker, Leicester (GB)

(73) Assignee: Greybull Innovation Ltd, Leicester (GB)

( * ) Notice: Subject to any disclaimer, the term of this patent is extended or adjusted under 35 U.S.C. 154(b) by 258 days.

(21) Appl. No.: 14/608,219

(22) Filed: Jan. 29, 2015

(65) Prior Publication Data

US 2015/0216721 A1 Aug. 6, 2015

(30) Foreign Application Priority Data

Feb. 3, 2014 (GB) .................................. 1401759.4

(51) Int. Cl.
| | | |
|---|---|---|
| *A61F 7/00* | (2006.01) | |
| *A61F 7/08* | (2006.01) | |
| *A61F 7/10* | (2006.01) | |
| *A61D 99/00* | (2006.01) | |
| *A61D 9/00* | (2006.01) | |
| *A61F 7/02* | (2006.01) | |

(52) U.S. Cl.
CPC ................. *A61F 7/08* (2013.01); *A61D 9/00* (2013.01); *A61D 99/00* (2013.01); *A61F 7/10* (2013.01); *A61F 7/106* (2013.01); *A61F 7/02* (2013.01); *A61F 2007/0219* (2013.01); *A61F 2007/0222* (2013.01); *A61F 2007/0269* (2013.01); *A61F 2007/0279* (2013.01); *A61F 2007/0293* (2013.01); *A61F 2007/108* (2013.01)

(58) Field of Classification Search
CPC ...... A61F 2007/0268; A61F 2007/0271; A61F 2007/029
See application file for complete search history.

(56) References Cited

U.S. PATENT DOCUMENTS 2,547,886 A * 4/1951 Poux ......................... A61F 7/02
607/112
3,506,013 A * 4/1970 Zdenek ..................... A61F 7/10
607/108

(Continued)

FOREIGN PATENT DOCUMENTS

| FR | 2880260 A1 | 7/2006 |
| JP | 2006067865 A | 3/2006 |

OTHER PUBLICATIONS amazon.com, "Heating & Cooling Pack by Thermal-Aid", Dec. 10, 2013.

*Primary Examiner* — Kaitlyn Smith
(74) *Attorney, Agent, or Firm* — Kilyk & Bowersox, P.L.L.C.

(57) ABSTRACT

The present invention relates to a heating and/or cooling assembly such as a heat pad. The assembly includes a plurality of modules articulated together by connection means so that the assembly can be manipulated by a user to adopt a desired profile. At least one of the modules contains a thermal store in the form of a solid, liquid or gel responsive to heating or cooling externally applied to the assembly so that the solid, liquid or gel is heated or cooled, respectively, and remains in a heated or cooled state for a prolonged period of time after the externally applied heating or cooling is removed.

14 Claims, 5 Drawing Sheets

(56) References Cited

U.S. PATENT DOCUMENTS

| | | | | |
|---|---|---|---|---|
| 3,900,035 A * | 8/1975 | Welch | A61F 7/10 | 607/108 |
| 4,326,533 A * | 4/1982 | Henderson | F25D 3/08 | 2/171.2 |
| 4,700,706 A * | 10/1987 | Munch | A61F 7/02 | 604/113 |
| 5,005,374 A * | 4/1991 | Spitler | A41D 13/0055 | 2/171.2 |
| 5,088,487 A * | 2/1992 | Turner | A61F 7/02 | 607/108 |
| 5,265,669 A * | 11/1993 | Schneider | A61F 7/02 | 165/46 |
| 5,848,981 A * | 12/1998 | Herbranson | A61F 7/10 | 601/134 |
| 5,957,964 A * | 9/1999 | Ceravolo | A61F 7/10 | 607/109 |
| 8,172,888 B1 * | 5/2012 | Beavers | A61F 7/02 | 607/104 |
| 2002/0042641 A1 * | 4/2002 | Johnson | A61F 7/02 | 607/114 |
| 2004/0267341 A1 | 12/2004 | Harrison | | |
| 2005/0228466 A1 * | 10/2005 | Harris | A61F 7/03 | 607/114 |
| 2008/0039913 A1 * | 2/2008 | Mizrahi | A61F 7/00 | 607/114 |
| 2008/0077211 A1 * | 3/2008 | Levinson | A61F 7/10 | 607/108 |
| 2008/0287839 A1 * | 11/2008 | Rosen | A61F 7/10 | 601/18 |
| 2010/0016933 A1 * | 1/2010 | Chen | A61F 7/02 | 607/112 |
| 2011/0040360 A1 * | 2/2011 | Subia | A61F 7/02 | 607/112 |
| 2011/0178585 A1 * | 7/2011 | Biser | A61F 7/02 | 607/109 |

* cited by examiner

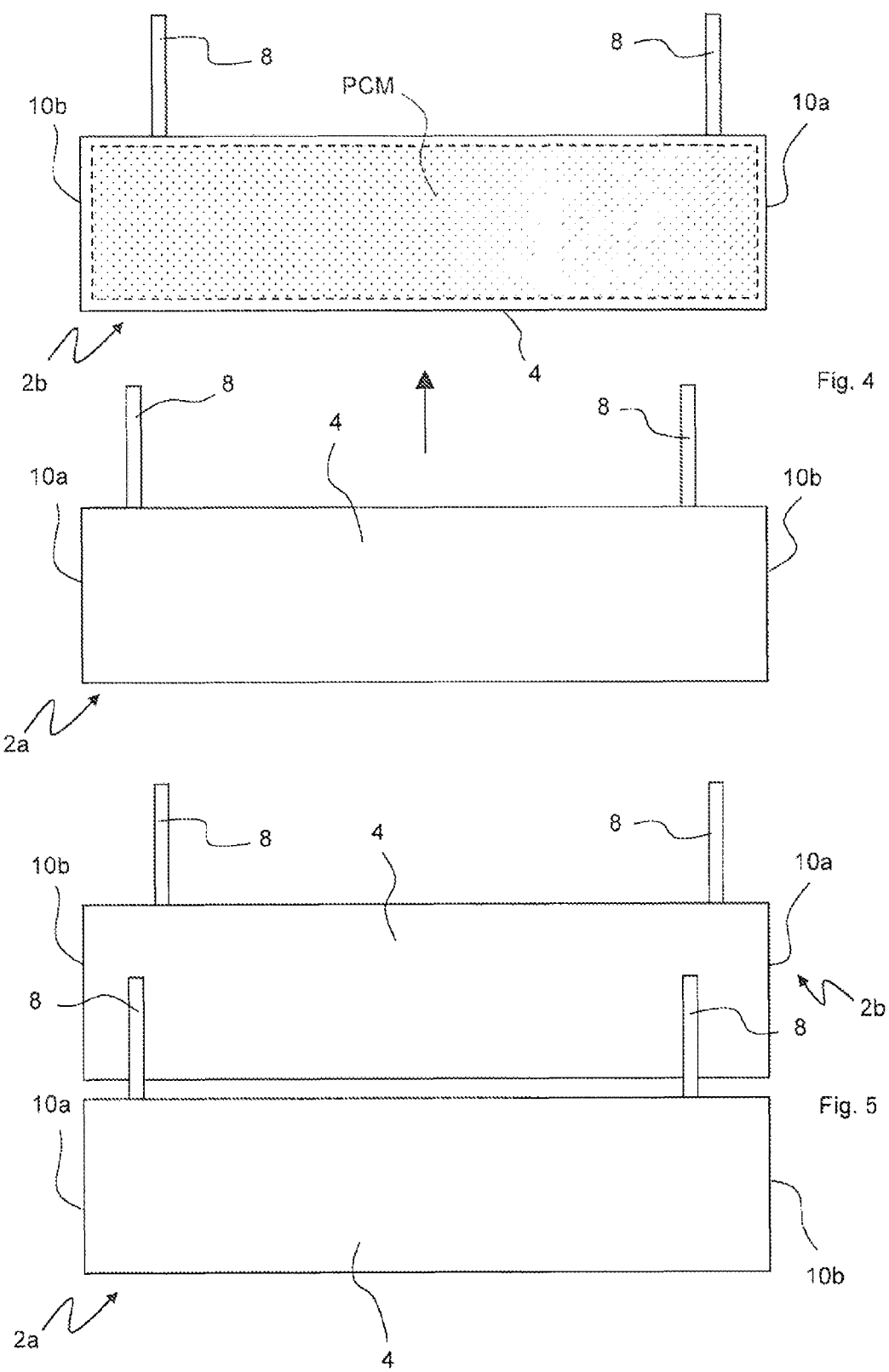

HEATING AND/OR COOLING ASSEMBLY

TECHNICAL FIELD

The present invention relates to a heating and/or cooling assembly, and in particular to a heating and/or cooling assembly that is inherently suitable for use with pets that are typically kept in hutches or enclosures such as rabbits, guinea pigs, chinchillas, degus, hamsters etc.

BACKGROUND ART

Heat pads for pets are known. One example is the Snugglesafe® heat pad that is disc-shaped, contains a non-toxic gel, and can be heated in a microwave. (The Snugglesafe® heat pad is supplied by Lenric C21 Ltd of Unit 10, Thorgate Road, Littlehampton, BN17 7LU, United Kingdom).

A fleece cover is typically provided to prevent the pet from coming into direct contact with the heat pad.

Existing heat pads such as the Snugglesafe® are not particularly satisfactory for use in hutches or enclosures. Because they are typically flat, the heat pad must be placed on the surface of the bedding (e.g., straw, hay or wood shavings), or buried within in. When the heat pad is removed, the bedding can be stuck to the fleece cover and it must be cleaned after being exposed to pet droppings, urine etc.

SUMMARY OF THE INVENTION

The present invention provides a heating and/or cooling assembly (e.g., a heat pad) comprising a plurality of modules articulated together by connection means so that the assembly can be manipulated by a user to adopt a desired profile, and wherein at least one of the modules contains a thermal store in the form of a solid, liquid or gel responsive to heating or cooling externally applied to at least part of the assembly (e.g., by placing the whole assembly, or just the at least one module that contains the thermal store, in a microwave or freezer) so that the solid, liquid or gel is heated or cooled, respectively, and remains in a heated or cooled state for a period of time after the externally applied heating or cooling is removed.

During the period of time (e.g., a period of a few minutes up to a prolonged period of several hours), the assembly can be used to provide heating or cooling.

The assembly can include any suitable number of modules.

The modules can be releasably connected together by the connection means. In other words, the modules can be separately formed and then connected together to define the assembly. The user can optionally connect together a desired number of modules to construct an assembly having a particular size.

Each module can include a connection part (optionally being integral with the module) that allows it to be connected to another module. Each module can include a substantially-rigid body or housing that encloses the solid, liquid or gel material of the thermal store or the supersaturated liquid or gel—see below. The body or housing can be made from a suitable plastics material using any suitable process, e.g., vacuum moulding, extrusion etc. The modules can be directly connected together such that adjacent modules that define the assembly are in direct, physical, contact with each other. The direct connection can utilise the connection part that can optionally be an integral part of the body or housing.

Substantially all of the modules within the assembly can have the same construction.

The connection part can be formed such that, when two modules are releasably connected together, their respective connection parts are not in register with each other so that they do not hinder relative movement between the adjacent modules. In one arrangement, this can be achieved even if all of the modules have the same construction, by connecting adjacent modules together in an opposite orientation.

In one arrangement, at least a pair of adjacent modules are rotatably connected together. In other words, the connection means (e.g., an integral connection part) allows one module to rotate relative to an adjacent module. The modules can therefore be manipulated into different profiles by rotating or repositioning the modules such that the connection part of each module, or some other part, adopts a particular angular orientation with respect to the corresponding part of an adjacent module. The connection means and/or the module body can be adapted to limit relative rotation between adjacent modules to just one rotational direction, i.e., relative rotation is not permitted in the opposite rotational direction, or to limit relative movement between adjacent modules to just one movement direction.

The connection means and/or the module body can be adapted to temporarily maintain the assembly in substantially the desired profile. For example, once the modules have been manipulated by the user to adopt a desired profile, the assembly can be effectively maintained in the desired profile by the connection means until the user wants to manipulate the modules to a different profile. Some sort of temporary or user-activated locking means or retaining means can be provided. In practice, it may be that the assembly is maintained in substantially the desired profile until a certain force is applied by the user, at which point the modules will be articulated to a different profile under the action of that applied force. For example, in the case of friction contact between adjacent modules, a force greater than the static friction force must be applied if the user wants the assembly to adopt a different profile. If the assembly is intended to be placed in a hutch or enclosure for use with pets such as rabbits, guinea pigs, chinchillas, degus, hamsters etc., the assembly will preferably maintain the desired profile even if the pet climbs on top of the assembly. In one arrangement, the connection means and at least part of the module body (e.g., the part of the module body that it is in contact with the connection means of an adjacent module when connected together) can be provided with a complementary engagement profile or engagement means to increase the amount of force necessary to manipulate the assembly so that the orientation of adjacent modules, and hence the overall assembly, can be selectively maintained. In one arrangement, one or both of the connection means and the outer surface of the module body might be formed with a saw-tooth or ridged profile or the like that still allows for relative rotation between the adjacent modules only when the necessary amount of force is applied. Such an engagement profile might also allow for relative rotation in one direction (e.g., clockwise) while completely preventing relative rotation in the opposite direction (e.g., counter-clockwise). In one arrangement, the engagement profile can include a series of flats or planar surfaces around the circumference of each module body or housing that are engaged by complementary planar surfaces of the connection means of an adjacent module. The complementary planar surfaces prevent relative movement between the adjacent modules to maintain the desired profile, and mean that adjacent modules can only be connected together at certain predetermined orientations. The predetermined orientations will depend on the number of flats or planar surfaces provided on each module.

Additional connection means can be provided at the axial ends of each module to allow modules to be connected together in the axial direction, i.e., end-to end. In one arrangement, one end of each module can be provided with a first (e.g., a 'male-type') connection means and the other end of each module can be provided with a complementary second (e.g., a 'female-type') connection means. Connecting together a number of modules side-by-side allows an assembly to be created with any desired length. If additional connection means are also provided then modules can be connected together end-to-end to allow an assembly to be created with any desired width.

In one arrangement, at least one of the modules does not contain a thermal store (or supersaturated liquid or gel see below). In other words, the assembly can comprise a first type of module that contains a thermal store for supersaturated liquid or gel) and a second type of module that does not contain a thermal store (or supersaturated liquid or gel). Providing different types of module allows the amount of heating or cooling provided by the assembly to be controlled. In other words, the assembly will provide less heating or cooling if it includes fewer modules of the first type or vice versa. If the modules are releasably connected together, the number of modules of the first and second types can be determined by the user. Modules of the second type allow the assembly to adopt the desired profile but do not actively contribute to the heating or cooling provided by the assembly.

The assembly can be manipulated to adopt any desired profile. For example, the assembly can be substantially flat (i.e., with a planar profile) so that it can be used like a conventional heat pad. In one arrangement, the desired profile can be substantially ∩-shaped so that the assembly forms an enclosed space in which small pets such as rabbits, guinea pigs, chinchillas, degus, hamsters etc. can conveniently shelter when the assembly is placed in a hutch or enclosure. It should be noted that such pets do not just require heating during cold weather. Some pets, and in particular guinea pigs, are unable to regulate their own body temperature, and can also require cooling during very hot weather.

Another desired profile can be substantially L-shaped. In this case the assembly can be placed in the corner of a hutch or enclosure with the L-shaped end in contact with the bedding or floor, and the apex of the assembly facing into the corner. Such ∩- and L-shaped profiles can be advantageous as compared to a planar profile because the majority of the assembly is held away from the bedding. Because the assembly is self-supporting, there is also no need to bury the assembly in the bedding.

It will be understood that these profiles are merely examples of the many different profiles that an assembly can adopt in practice.

The modules can be formed of any suitable material (e.g., a plastics material) and are typically substantially rigid. The modules can have any suitable shape, size, cross-section etc. and can include a cavity for the thermal store (or supersaturated liquid or gel—see below). Where modules are provided that do not contain a thermal store (or supersaturated liquid or gel) they can either be solid or include an air cavity. It is anticipated that external heating or cooling will be applied to such modules, i.e., to the assembly as a whole, but if the modules are releasably connected it may be possible to apply external heating or cooling to only those modules that contain a thermal store before connecting the different types of module together to construct the overall assembly.

The solid, liquid or gel that forms the thermal store can have any suitable composition and is preferably non-toxic so that it is suitable for use with pets. An example would be a gel composition using inter aka Carbopol®, propylene glycol, glycerine, ethyl paraben and water. Other suitable compositions, such as those used in conventional 'hot and cold' pads, will be known to the skilled person. Any suitable phase change materials where heat is absorbed or released when the material changes from a solid to a liquid, or vice versa, can be used as the thermal store. Non phase change materials can also be used. In general, the term 'thermal store' should be interpreted broadly to include any solid, liquid or gel material that is capable of storing thermal energy and subsequently releasing the stored thermal energy to provide practically useful heating or cooling for a period of time after the externally applied heating or cooling is removed.

In an alternative assembly, the at least one module can contain a supersaturated liquid or gel (e.g., sodium acetate trihydrate) instead of the thermal store, and preferably also means (e.g., a trigger device that provides a nucleation site) for allowing the user to selectively initiate crystallisation of the supersaturated liquid or gel to release heat energy for a period of time. Again, the liquid or gel is preferably non-toxic. The at least one module can be reset by heating until all of the crystals have melted. Such modules generate their own heat energy as a result of the crystallisation process and external heating does not need to be applied. The present invention further provides a heating assembly comprising a plurality of modules articulated together by connection means so that the assembly can be manipulated by a user to adopt a desired profile, and wherein at least one of the modules contains a supersaturated liquid or gel and means for allowing the user to selectively initiate crystallisation of the supersaturated liquid or gel to release heat energy for a period of time. Other features of the modules are as described herein.

The assembly can be covered by a cover in use to prevent direct contact with the heated or cooled modules. The cover can optionally be adapted to cover different sized assemblies that the user can optionally construct from a different number of releasable modules. A non-fleece cover might be preferred if the assembly is going to be used in a hutch or enclosure where the bedding might stick or adhere to the fleece material. In this case, a cover with a waterproof or wipe-clean outer layer might be preferred. The cover can include an insulating inner layer. The assembly can also be placed inside a bag (e.g., a slide-lock bag) or other container for hygiene purposes before being placed in a microwave or freezer.

In one arrangement, the assembly can be heated or cooled for a particular period of time. For example, the assembly can be placed in a microwave (where the heating time will depend on the power of the microwave) or in a freezer. If the modules can be releasably connected together, and only certain modules contain a thermal store, then only these modules need to be heated or cooled. But it is anticipated that the whole assembly will typically be heated or cooled, including any modules that do not contain a thermal store. This will certainly be the case if the modules are integrally connected together.

The assembly is then removed from the microwave or freezer (or the modules are removed and connected together to construct an assembly).

The user can manipulate the assembly to a desired profile. (This manipulation can be done before or after the external heating or cooling has been applied, and before or after the assembly has been covered with the optional cover.)

The assembly can be manipulated into a particular profile (e.g., a compact profile) to allow it to fit inside the microwave or freezer, before being manipulated into its final desired profile once it has been heated or cooled.

An optional cover can be placed over the assembly.

The assembly can then be placed wherever it is needed to provide heating or cooling, e.g., space heating or cooling within a hutch or enclosure, or direct heating or cooling of a pet.

Each thermal store will remain in a heated or cooled state for a period of time after the assembly (or modules) have been removed from the microwave or freezer.

The invention further provides a plurality of modules being adapted to be connected together to construct a heating and/or cooling assembly that can be manipulated by a user to adopt a desired profile, and wherein at least one of the modules contains a thermal store in the form of a solid, liquid or gel responsive to heating or cooling externally applied to the at least one module so that the solid, liquid or gel is heated or cooled, respectively, and remains in a heated or cooled state for a period of time after the externally applied heating or cooling is removed.

The present invention further provides a plurality of modules being adapted to be connected together to construct a heating assembly that can be manipulated by a user to adopt a desired profile, and wherein at least one of the modules contains a supersaturated liquid or gel and means for allowing the user to selectively initiate crystallisation of the supersaturated liquid or gel to release heat energy for a period of time.

Other features of the modules are as described herein.

DRAWINGS

FIG. 4 is a top view of the pair of modules of FIG. 1;

FIG. 5 is a top view of the pair of modules of FIG. 1 connected together;

Figure 1:
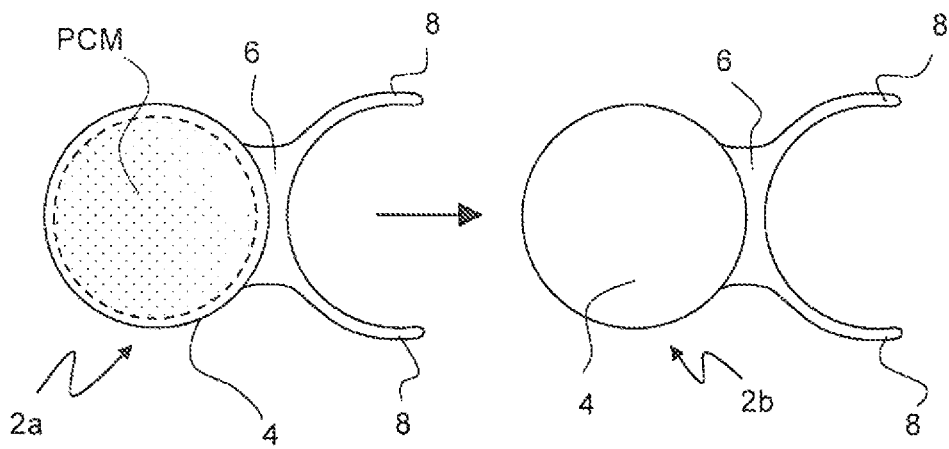
FIG. 1 is a side view showing a pair of modules that can be connected together to form an assembly according to the present invention.

With reference to FIGS. 1 and 4, a module 2 for constructing a heating and/or cooling assembly 1 according to the present invention includes a substantially cylindrical body 4 made of a suitable plastics material that contains a thermal store, e.g., in the form of a non-toxic gel composition. In an alternative arrangement (not shown) a module can contain a non-toxic supersaturated liquid or gel (e.g., sodium acetate trihydrate) and a trigger device that, when activated by the user, provides a nucleation site that initiates crystallisation of the supersaturated liquid or gel into a solid.

The module 2 includes a pair of integral connection parts 6 each having a pair of curved, resilient, arms 8. The connection parts 6 are spaced apart along the axial direction of the module 2 and each connection part is a different distance from the respective axial end of the module.

Figure 2:
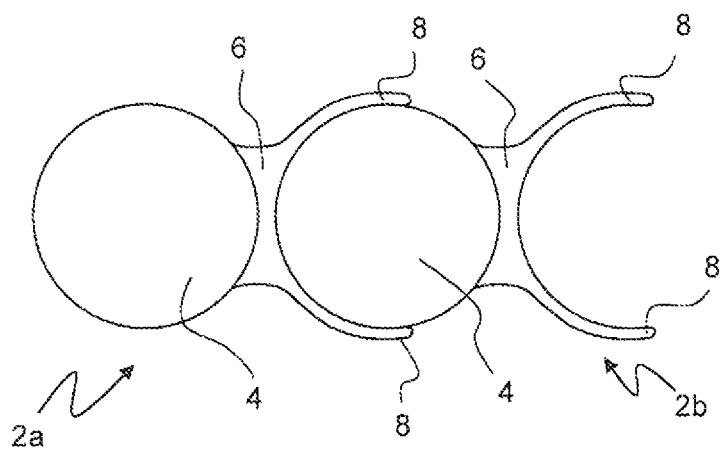
FIG. 2 is a side view of the pair of modules of FIG. 1 connected together.

A plurality of modules 2 can be connected together using the connection parts 6 to form an assembly. FIGS. 1 and 2 show how a pair of modules 2a, 2b can be connected together. The arms 8 are shaped to have an inner profile that corresponds to the outer profile of the body 4. The arms 8 of module 2a will flex outwardly as the adjacent module 2b is pushed into module 2a and then return to their initial position were they are in friction contact with the outer surface of the body 4 of the adjacent module 2b. It will be readily understood that a third module can be pushed into module 2b, and so on, until an assembly containing the desired number of identical modules has been constructed.

As discussed above, not all of the modules need to contain a thermal store and their bodies can be substantially hollow.

Figure 3:
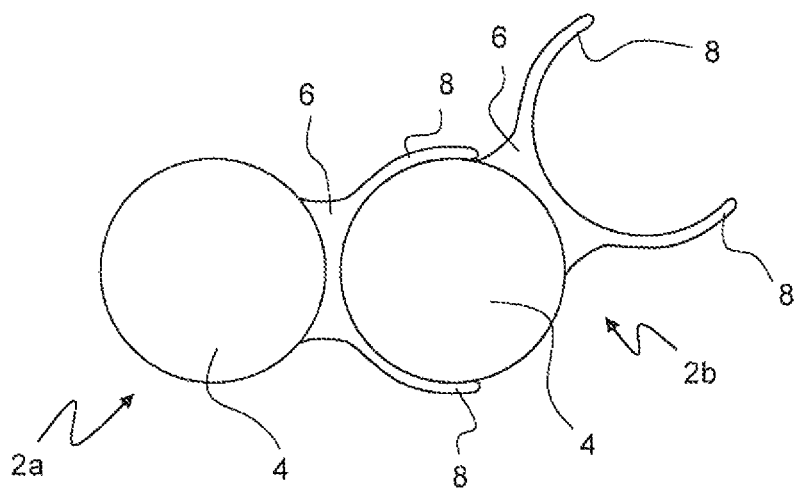
FIG. 3 is a side view of the pair of modules of FIGS. 1 and 2 rotated relative to each other to adopt a particular angular orientation.

Adjacent modules can be rotated relative to each other. This is shown in FIG. 3 where module 2b has been rotated relative to the connection parts 6 of module 2a so that the connection parts of the adjacent modules adopt a particular angular orientation with respect to each other.

Figure 10:
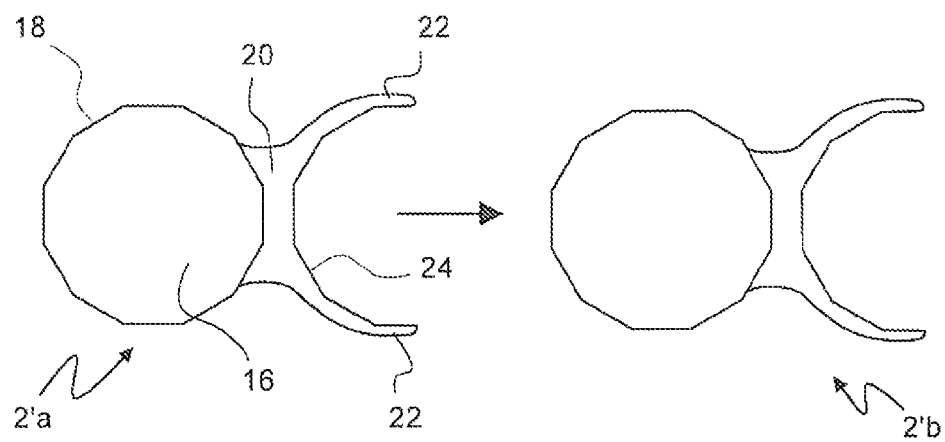
FIG. 10 is a side view showing a pair of alternative modules that can be connected together to form an assembly according to the present invention.

The modules can be constructed to temporarily retain adjacent modules in a particular angular orientation. In one arrangement the angular orientation can be temporarily maintained simply by a friction fit between the connection parts 6 and the outer surface of the body 4 of the adjacent module. But it will be readily appreciated that in some cases a friction fit will not be sufficient. For example, it might be necessary or desirable to increase the amount of force that needs to be applied by the user to move the adjacent modules to a particular angular orientation, and to thereby more securely retain the adjacent modules in the angular orientation. In one arrangement, one or both of the connection part and the outer surface of the body might be formed with engagement means or an engagement profile (e.g., a sawtooth or ridged profile or the like) that still allows for relative rotation between the adjacent modules when the necessary amount of force is applied to overcome the engagement. Such engagement means might also allow for relative rotation in one direction (e.g., clockwise) while completely preventing relative rotation in the opposite direction (e.g., counter-clockwise). In one arrangement, shown in FIGS. 10 to 12 an alternative module 2' includes a body 16 and a pair of integral connection parts 20 each having a pair of arms 22. (It will be readily appreciated that only one of the connection parts 20 is visible in FIGS. 10 to 12 but that the overall construction of module 2' is similar to the modules 2 shown in FIGS. 1 to 4.) An engagement profile includes a series of flats or planar surfaces 18 around the circumference of each body 16 that are engaged by complementary planar surfaces 24 of the connection part of an adjacent module. The complementary planar surfaces 18, 24 prevent relative movement between the adjacent modules to maintain the desired profile, and mean that adjacent modules can only be connected together at certain predetermined orientations. The predetermined orientations will depend on the number of flats or planar surfaces provided on each module. In the arrangement shown in FIGS. 10 to 12 the body 16 has twelve planar surfaces 18 but any suitable number can be provided. The flats or planar surfaces can extend along the full axial length of the body, or can be provided only in the part of the body which is contacted by the connection part of the adjacent module. If engagement means are provided on one or both of the connection part and the outer surface of the body, such engagement means can be conveniently disengaged by disconnecting the modules from each other.

Figure 11:
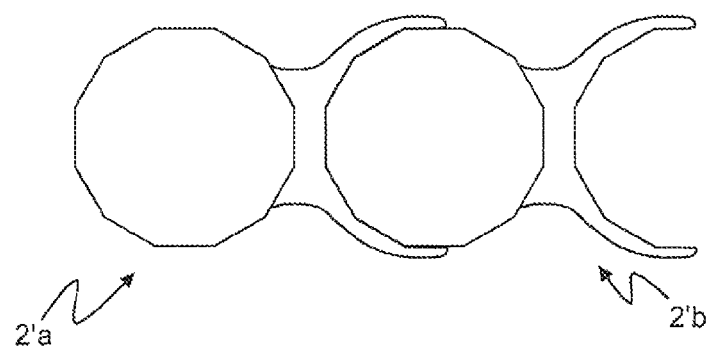
FIG. 11 is a side view of the pair of modules of FIG. 10 connected together.
Figure 12:
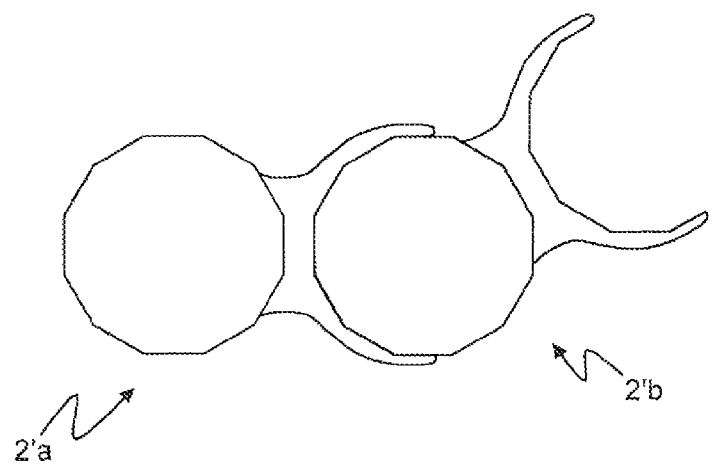
FIG. 12 is a side view of the pair of modules of FIGS. 10 and 11 rotated relative to each other to adopt a particular angular orientation.

The engagement means or profile can also be used to prevent relative rotation between the adjacent modules unless the modules are unconnected and then re-connected in a different angular orientation, e.g., as shown in FIGS. 11 and 12 with adjacent modules 2'a and 2'b.

It is convenient (from a point of view of manufacturing cost) if all of the modules have the same construction. FIGS. 4 and 5 show how the connection parts 6 can be formed so that they do not hinder relative rotation between the adjacent modules 2a, 2b. The connection parts 6 are asymmetrically located. The connection parts 6 are therefore not in register when the adjacent modules 2a, 2b are connected together in an opposite orientation. More particularly, each module has a first end 10a and a second end 10b. As shown in FIGS. 4 and 5, the first module 2a has its first end 10a on the left-hand side and its second end 10b on the right-hand side. The second module 2b has the opposite orientation, with its first end 10a on the right-hand side and it second end 10b on the left-hand side.

Because the connection parts 6 are not in register, the adjacent modules 2a, 2b can undergo relative rotation over a large angle, e.g., with reference to FIG. 3, until the connection part 6 of module 2b comes into contact with the outer surface of the body 4 of module 2a.

Although the connection parts 6 are shown as being relatively narrow, it will be readily appreciated that they can be formed with any suitable width. Other forms of connection means can also be provided, including those where the modules are integrally connected together and are not releasable.

Figure 6:
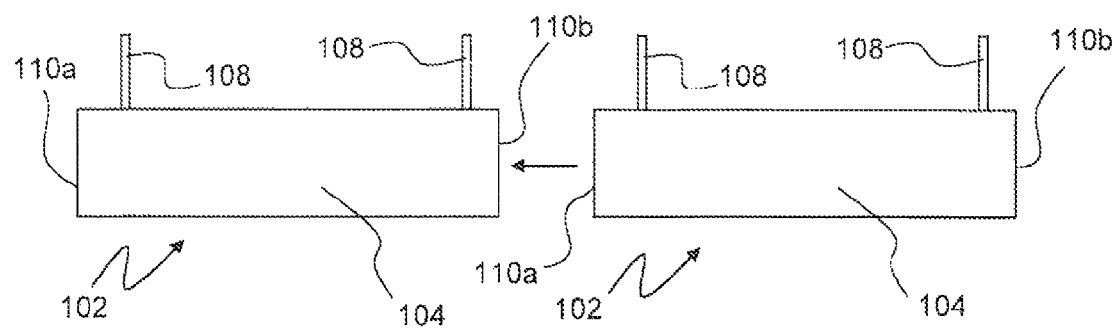
FIG. 6 is a top view showing a pair of alternative modules that can be connected together to form an assembly according to the present invention.
Figure 7:
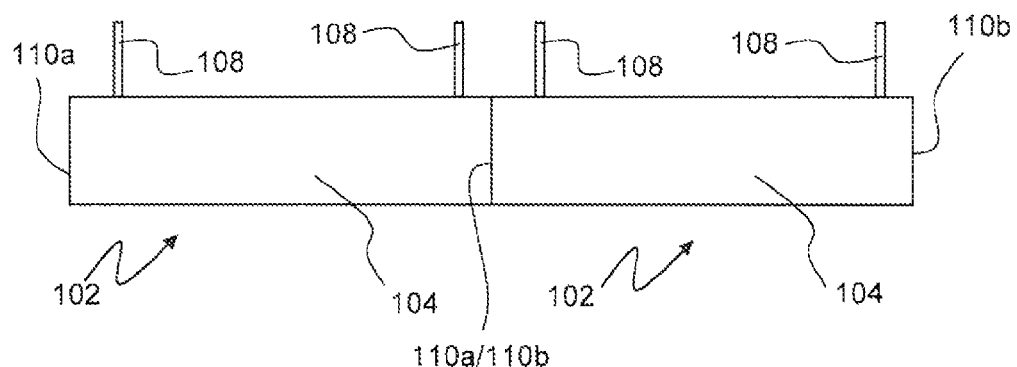
FIG. 7 is a top view of the pair of modules of FIG. 6 connected together.

An alternative module 102 is shown in FIGS. 6 and 7. The alternative module 102 is similar to the module 2 described above and include a substantially cylindrical body 104 made of a suitable plastics material that contains a thermal store, e.g., in the form of a gel composition. The module 102 includes a pair of integral connection parts each having a pair of curved, resilient, arms 108. A plurality of modules 102 can be connected together using the connection parts as described above to form an assembly.

In addition to the resilient arms 108, each module 104 includes a male connector at a first end 110a and a female connector at a second end 110b. The male and female connectors 110a, 110b can have any suitable construction and allow modules to be releasably connected together end-to-end as shown in FIG. 7. It will be readily appreciated that the modules 102 can also be connected together side-by-side using the resilient arms 108 in the same manner as the modules 2. In one arrangement, a plurality of modules 102 can be connected together using the arms 108 to form a first sub-assembly and a plurality of modules can be connected together using the arms to form a second sub-assembly. The sub-assemblies can then be connected together using the male and female connectors 110a, 110b.

Figure 8:
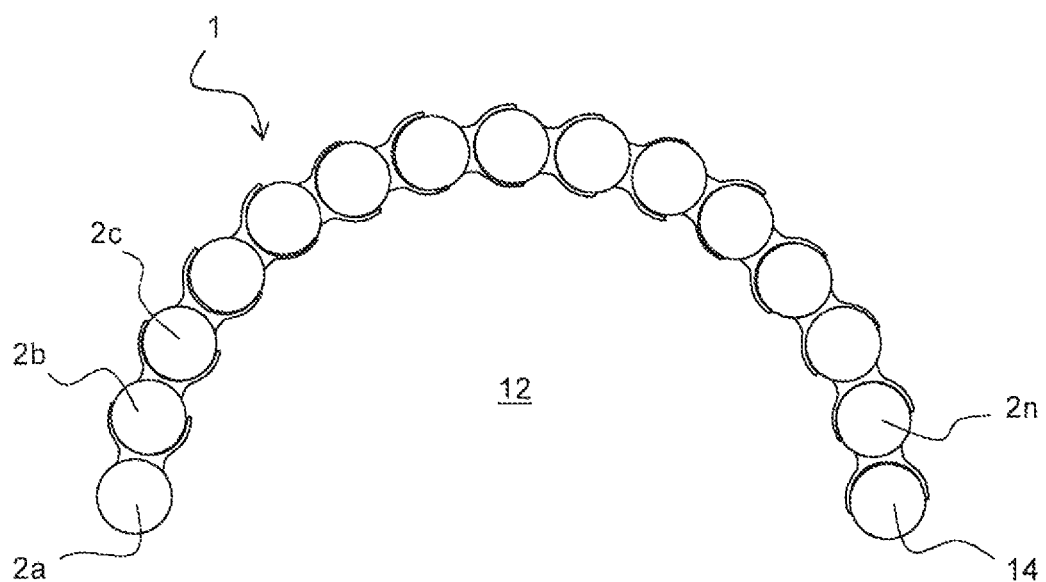
FIG. 8 is a side view of an assembly according to the present invention in a substantially ∩-shaped profile.
Figure 9:
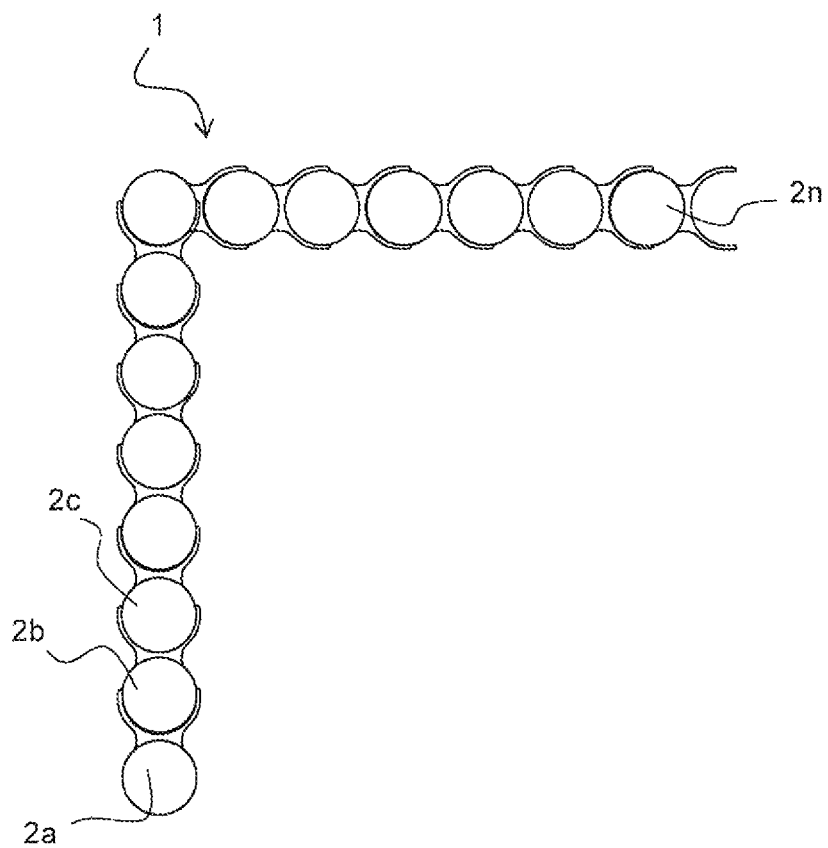
FIG. 9 is a top view of an assembly according to the present invention in a substantially L-shaped profile.

With reference to FIGS. 8 and 9, an assembly 1 is constructed from a plurality of modules 2a-2n (or modules 102) all having the same construction and connected together as described above.

Once the modules have been connected together, they can be manipulated by the user to adopt different profiles.

FIG. 8 shows the assembly 1 with a substantially ∩-shaped profile where the assembly 1 forms an enclosed space 12 in which pets such as rabbits, guinea pigs, chinchillas, degus, hamsters etc. can conveniently shelter when the assembly is placed in a hutch or enclosure. The assembly 1 shown in FIG. 8 also includes an end module 14 with a substantially cylindrical body but no connection means. Such an end module 14 is entirely optional but makes the overall assembly more symmetrical in appearance and can prevent the connection means 6 from being damaged.

FIG. 9 shows the assembly 1 with a substantially L-shaped profile which can be fitted into a corner of a hutch or enclosure. (In FIG. 9 it will be understood that the assembly 1 is being viewed from above, i.e., looking down towards the floor of the hutch or enclosure.)

All of the modules 2a-2n can contain a thermal store. But in one arrangement, only some of the modules will contain a thermal store and the body of the remaining modules will be empty or formed of a solid material.

The assembly 1 can be covered by a fleece cover (not shown).

The assembly 1 can be heated or cooled, e.g., by placing the assembly in a microwave or freezer. The heated or cooled thermal stores will remain in a heated or cooled state for a period of time, during which the assembly 1 can be used to provide heating or cooling, respectively.

What is claimed is:

1. A heating and/or cooling assembly for heating or cooling a pet enclosure, the assembly comprising a plurality of modules, each module comprising a substantially-rigid body having a circumference, the modules being articulated and connected together by connection parts so that the assembly can be manipulated by a user to adopt a desired profile, wherein the connection parts and at least part of the body of each module are provided with a complementary engagement profile to substantially maintain the assembly in the desired profile, wherein the complementary engagement profile includes a series of planar surfaces around the circumference of each body and complementary planar surfaces on each connection part, and wherein at least one of the modules contains a thermal store in the form of a solid, liquid or gel responsive to heating or cooling externally applied to at least part of the assembly so that the solid, liquid or gel is heated or cooled, respectively, and remains in a heated or cooled state for a period of time after the externally applied heating or cooling is removed.

2. The assembly of claim 1, wherein the connection parts are integral parts of the bodies.

3. The assembly of claim 1, wherein at least one of the modules does not contain a thermal store.

4. The assembly of claim 1, covered by a cover.

5. The assembly of claim 1, wherein the solid, liquid or gel of the thermal store is a phase change material.

6. The assembly of claim 1, wherein the plurality of modules comprises an end module that does not comprise any of the connection parts.

7. The assembly of claim 1, wherein all but one of the modules, of the plurality of modules, comprises an integral connection part.

8. A plurality of modules being adapted to be connected together to construct a heating and/or cooling assembly for heating or cooling a pet enclosure and that can be manipulated by a user to adopt a desired profile, wherein each module comprises a substantially-rigid body having a circumference, and a connection part that allows it to be connected directly to another module, wherein the connection part and at least part of the body are provided with a complementary engagement profile that includes a series of planar surfaces around the circumference of the body, and complementary planar surfaces on the connection part, and wherein at least one of the modules contains a thermal store in the form of a solid, liquid or gel responsive to heating or cooling externally applied to the at least one module so that the solid, liquid or gel is heated or cooled, respectively, and remains in a heated or cooled state for a period of time after the externally applied heating or cooling is removed.

9. The plurality of modules of claim 8, wherein each module has the same construction.

10. The plurality of modules of claim 8, wherein each connection part is an integral part of the respective body.

11. The plurality of modules of claim 8, wherein the solid, liquid or gel of the thermal store is a phase change material.

12. A plurality of modules being adapted to be connected together to construct a heating and/or cooling assembly for heating or cooling a pet enclosure and that can be manipulated by a user to adopt a desired assembly profile, wherein each module comprises a substantially-rigid body and a connection part that allows it to be connected directly to another module, wherein, for each module, the connection part and at least part of the body are provided with complementary engagement profiles that include a series of planar surfaces around a circumference of the body and complementary planar surfaces on the connection part, and wherein at least one of the modules contains a supersaturated liquid or gel and a trigger device for allowing the user to selectively initiate crystallisation of the supersaturated liquid or gel to release heat energy for a period of time.

13. A heating and/or cooling assembly for heating or cooling a pet enclosure, the assembly comprising the plurality of modules of claim 12, wherein the modules are articulated and connected together by the connection parts so that the assembly can be manipulated by a user to adopt a desired assembly profile and the modules substantially maintain the assembly in the desired assembly profile.

14. The assembly of claim 13, further comprising an end module that does not include a connection part.

\* \* \* \* \*